United States Patent [19]

Windawi et al.

[11] Patent Number: 4,483,943
[45] Date of Patent: Nov. 20, 1984

[54] GAS CONVERSION CATALYSTS

[75] Inventors: Hassan Windawi, Arlington Heights; Michael H. Quick, Palatine, both of Ill.

[73] Assignee: UOP Inc., Des Plaines, Ill.

[21] Appl. No.: 483,039

[22] Filed: Apr. 7, 1983

[51] Int. Cl.³ .................... B01J 21/04; B01J 23/06; B01J 23/22; B01J 23/72
[52] U.S. Cl. .................................... 502/342; 518/713
[58] Field of Search ............. 502/307, 324, 342, 343; 518/713

[56] References Cited

U.S. PATENT DOCUMENTS 3,897,471  7/1975  Herbert et al. ............. 502/324 X
4,107,089  8/1978  Bondar et al. ................. 502/307

FOREIGN PATENT DOCUMENTS 1302726  1/1973  United Kingdom.
238527   3/1969  U.S.S.R. ............................. 502/342

Primary Examiner—W. J. Shine
Attorney, Agent, or Firm—James R. Hoatson, Jr.; Raymond W. Nelson; William H. Page, II

[57] ABSTRACT

Gas conversion catalysts which possess a high resistance to catalyst poisoning such as sulfur and/or chlorine-containing compounds, comprise a catalyst composite of copper, zinc and aluminum compounds containing at least one metal selected from the metals consisting of groups IVB, VB, VIB and VIIB of the Periodic Table. This catalyst composition may be used to synthesize methanol from a feedstock of carbon monoxide and hydrogen.

2 Claims, No Drawings

GAS CONVERSION CATALYSTS

BACKGROUND OF THE INVENTION

Catalyst composites which are utilized for the conversion of gases into useable products such as in the synthesis of methanol or water-gas shift reactions have comprised mixtures of copper, zinc and aluminum. However, a major problem which is associated with the use of these catalysts in the aforesaid reactions lies in their high sensitivity to poisons such as sulfur and chlorine. The sulfur and chlorine are usually present in the gaseous feedstocks which are utilized to effect the reaction, such gaseous feedstocks being derived from natural gas, the gasification of coal or the by-products from the refining of heavy oil, said gases being generally referred to as synthetic gases. In order to effectively utilize these catalysts in commercial operations, it is necessary that sulfur and chlorine guard beds be employed in order to reduce the level of the sulfur and chlorine to a range of about 10 parts ber billion (ppb).

The removal of these poisons such as sulfur is required due to the high affinity of the zinc component of the catalyst composite for sulfur, said affinity causing structural composition changes that lead to deactivation. Due to the high affinity of the metals for the poisons such as sulfur or chlorine, a build-up of the poison on the surface of the active metals will lead to the aforesaid deactivation of the catalyst. In view of this, it is therefore desirable to enhance the stability of the catalyst when utilizing such catalyst in a continuous commercial operation whereby the life of the catalyst is substantially lengthened or enhanced to a point where it is commercially feasible to operate the desired process. The stability and activity of the catalyst may be enhanced by the addition of certain components to the catalyst system whereby higher sulfur levels in the feedstock may be accommodated without requiring the presence of the aforesaid sulfur or chlorine guard beds, thus simplifying the overall design plan of the reaction process with a concurrent lower expense to operate the reaction process and obtain the desired product.

As will hereinafter be shown in greater detail, by employing the novel catalyst system of the present invention, it is possible to obtain results of high catalyst activity and more extensive stability of the same.

BRIEF SUMMARY OF THE INVENTION

This invention relates to novel catalyst systems which may be employed for the conversion of gases to useable products. More specifically, the invention is concerned with a novel catalyst system for the synthesis of methanol from a gaseous feedstock whereby greater activity and longer catalyst life will be a contributing factor to the success of the operation.

It is well known that methanol is an important chemical compound which finds a wide variety of uses. For example, methanol may be used in the production of formaldehyde, as an automotive antifreeze, as an intermediate in the chemical synthesis of other compounds such as methylamine, methacrylate, etc., as a general solvent, and a paint remover, as a denaturant for ethyl alcohol, for rocket fuel, etc. One particular use for methanol is as a fuel for internal combustion engines, being used for the production of methyl-t-butyl ether which is an additive for gasoline to impart desirable characteristics such as octane numbers to the gasoline. One process for obtaining methanol involves the synthesis of the product by reacting carbon monoxide and hydrogen in the presence of certain catalytic compositions of matter at elevated temperatures and pressure to produce the aforesaid methanol.

It is therefore an object of this invention to provide a catalyst system which may be used in the conversion of gases to useable products.

A further object of this invention is to provide a process for obtaining methanol by reacting carbon monoxide and hydrogen in the presence of a novel catalyst system.

In one aspect an embodiment of this invention resides in a catalyst for the conversion of gases to useable products which comprises a solid composite of copper, zinc and aluminum compounds containing at least one metal selected from the metals consisting of Groups IVB, VB, VIB and VIIB of the Periodic Table.

Another embodiment of this invention is found in a process for the synthesis of methanol which comprises treating a mixture of carbon monoxide and hydrogen at reaction conditions in the presence of a catalyst system comprising a solid composite of copper, zinc and aluminum compounds containing at least one metal selected from the metals of Groups IVB, VB, VIB, and VIIB of the Periodic Table, and recovering covering the resultant methanol.

A specific embodiment of this invention is found in a catalyst for the conversion of gases to useable products which comprises a solid composite of copper, zinc and aluminum containing from about 0.01 to about 1% by weight of tungsten.

Another specific embodiment of this invention is found in a process for the synthesis of methanol which comprises treating a mixture of carbon monoxide, carbon dioxide and hydrogen at a temperature in the range of from about 200° to about 400° C. and a pressure in the range of from about atmospheric to about 100 atmospheres in the presence of a solid composite of copper, zinc and aluminum compounds which contains from about 0.01% to about 1% by weight of tungsten, and recovering the resultant methanol.

Other objects and embodiments will be found in the following further detailed description of the present invention.

DETAILED DESCRIPTION OF THE INVENTION

As hereinbefore set forth, the present invention is concerned with a novel catalyst system which is utilized for the conversion of gases to useable products. The catalyst composite, which will possess relatively good stability and excellent longevity with regard to catalytic activity, will comprise a solid composite of copper, aluminum, and zinc compounds containing from about 0.01% to about 1% by weight of a metal or metal compound selected from the metals of the groups IVB, VB, VIB and VIIB of the Periodic Table. Specific examples of these metals which may be employed to impart the desirable characteristics to the catalyst composite will include titanium, zirconium, hafnium, vanadium, niobium, tantalum, chromium, molybdenum, tungsten, manganese and rhenium. The presence of this metal will inhibit the poisoning of the catalyst system due to the presence of sulfur and/or chlorine in the gaseous feedstock and will thus enable the catalyst to be utilized for a longer period of time in gas conversion reactions.

The desired catalyst system may be prepared in any suitable manner. One type of operation which may be employed to prepare the catalyst of the present invention is to coprecipitate soluble salts of copper, aluminum and zinc to obtain a solid catalyst composite. The solid catalyst composite may contain from about 40% to about 60% by weight of copper, about 5% to about 10% by weight of aluminum and from about 10% to about 20% by weight of zinc, the remainder of the catalyst composite comprising the inorganic salt portion of the system. After precipitation, the solid composite may be recovered, aged at an elevated temperature in the range of from about 50° to about 75° C. and dried at an elevated temperature in excess of about 100° C. for a period of time sufficient to remove all traces of water which may still be present. Following this, the catalyst composite may then be impregnated with an aqueous or nonaqueous solution of an appropriate compound containing the metals of groups IVB, VB, VIB and VIIB of the Periodic Table. After impregnation of the solid composite for a predetermined period of time which may range from about 0.5 up to 10 hours or more in duration, the excess solution is recovered and the composite may then be calcined at a temperature in the range of from 250° to about 300° C. in an inert atmosphere provided for by the presence of an inert gas such as nitrogen, argon, helium, etc., and recovered.

Examples of soluble salts of copper, aluminum and zinc which may be used as starting materials to prepare the catalyst of the present invention will include copper nitrate, aluminum nitrate, zinc nitrate, copper acetate, aluminum acetate, zinc acetate, etc. Although there are other water-soluble salts of copper, zinc and aluminum such as the halides and sulfates, it is not feasible to utilize these compounds or salts inasmuch as a possible contamination or poisoning of the finished catalyst may occur. The precipitation of these salts is effected by treating the salts in an aqueous solution with a precipitating agent such as sodium carbonate, potassium carbonate, lithium carbonate, ammonium carbonate, etc. to obtain a solid composite of the salts of copper, zinc and aluminum.

Some specific examples of salts of metals of groups IVB, VB, VIB and VIIB of the Periodic Table which are utilized to impregnate the solid composite will include salts which are soluble in either an aqueous or nonaqueous solvent such as ammonium molybdate, ammonium vanadate, ammonium octamolybdate, ammonium paratungstate, molybdenum carbonyl, tungsten carbonyl, vanadium carbonyl, heteropoly acids such as tungstosilicic acid, molybdophosphoric acid, vanadomanganic acid, tungstogermanic acid, tungstocobaltic acid, molybdozirconic acid, molybdotitanic acid, molybdochromic acid, etc., chromium acetate, chromium nitrate, ammonium chromate, ammonium dichromate, chromium carbonyl, chromium acetylacetonate, manganese acetate, manganese nitrate, manganese carbonyl, manganese acetylacetonate, cyclopentadienyl manganese tricarbonyl, titanium methoxide, titanium ethoxide, titanium nitrate, dicyclopentadienyl titanium dicarbonyl, ammonium perrhenate, perrhenic acid, rhenium carbonyl, cyclopentadienyl rhenium tricarbonyl, zirconium tetrakisacetylacetonate, zirconium tetraacetate, zirconium nitrate, tetracyclopentadienyl zirconium, titanium tetrakisacetylacetonate, hafnium tetraacetate, tetracyclopentadienyl hafnium, cyclopentadienyl niobium tetracarbonyl, tetrabutylammonium pentacarbonyl niobate, cyclopentadienyl tantalum tetracarbonyl, tetrabutylammonium pentacarbonyl tantalate.

It is to be understood that the aforementioned salts of the metals of groups IVB, VB, VIB and VIIB of the Periodic Table are only representative of the class of compounds which may be employed to impregnate the solid composite of copper, zinc and aluminum to afford the desired additive to said composite, and that the present invention is not necessarily limited thereto.

The gas conversion catalyst of the present invention may be prepared in any suitable manner, either in a batch type or continuous type operation. For example, when a batch type operation is employed to prepare the desired compound, the required amounts of copper, zinc and aluminum salts such as copper nitrate, zinc nitrate, and aluminum nitrate are dissolved in an appropriate amount of distilled water. A separate solution of the precipitating agent such as sodium carbonate, ammonium carbonate, etc. in water is also prepared. The separate solutions are then heated to a temperature which may range from about 40° to about 95° C. and admixed at this temperature with vigorous stirring to form the precipitate. Following the precipitation, the pH of the mixture is adjusted to a range of from about 7.0 to about 7.2 and, after being allowed to age at an elevated temperature for a period which may range from about 10 minutes to about 1 hour or more in duration, the precipitate is filtered and washed with water. The solid comprising a composite of copper, zinc and aluminum salts is then dried at a temperature in excess of 100° C., that is, from about 110° to about 125° C. in an appropriate apparatus such as an oven and, after drying, is broken into pieces. The solid pieces are then water washed to remove any residue content cation such as sodium, potassium, ammonium, etc. from the solid and the washed material is then again dried at a temperature in the range hereinbefore set forth for a similar period.

The additive or modifier compound is then added to the catalyst composite by impregnation from a solution of the modifier. The impregnation of the catalyst composite may be accomplished utilizing an aqueous solution of a water-soluble salt of the metal selected from the groups IVB, VB, VIB and VIIB of the Periodic Table or, if so desired, the metal salt from this group may be dissolved in an appropriate organic solvent, said solvent including alcohols such as methanol, ethanol, propanol, etc.; ethers such as diethyl ether, dipropyl ether; paraffins such as pentane, heptane, hexane etc.; cycloparaffins such as cyclopentane, cyclohexane, methylcyclopentane, etc.; aromatic hydrocarbons such as benzene, toluene, the xylenes, etc.; acetone, acetonitrile, etc. It is to be understood that the choice of solvent will depend upon the nature of the metal compound which acts as the modifier for the catalyst composite. The desired amount of modifier compound sufficient to impart a modifier metal content of from about 0.01% to about 1% by weight of the catalyst composite is dissolved in the appropriate solvent and the solution is added to the solid catalyst composite in an appropriate apparatus. For example, the solution may be added to the composite in a round bottom flask which is mounted on a rotary vacuum evaporator. After subjecting the flask to rotation for a period which may range from about 10 to about 30 minutes at ambient temperature, the flask and contents thereof are heated to a temperature which may range from about 30° to about 90° C. under a reduced pressure to effect a slow evaporation of the solvent. Upon completion of the evaporation of the solvent, the modified catalyst composite may then be dried in an oven at a temperature from about 110° to about 115° C. for a period which may range from about 10 minutes to about 1 hour in duration.

The dried modified catalyst composite is then calcined at an elevated temperature which may range from about 200° to about 300° C. in a flowing nitrogen atmosphere for a period of time ranging from about 4 to about 24 hours in duration to obtain the desired gas conversion catalyst.

It is also contemplated within the scope of this invention that the gas conversion catalyst may be prepared in a continuous manner of operation. When this type of operation is employed, the solution containing soluble salts of copper, zinc and aluminum is continuously charged to a reactor which is maintained at the proper operating conditions of temperature and pressure. In addition, the solution of the precipitant is also continuously charged to the reactor wherein it contacts the first-named solution. After passage through the reactor for a predetermined period of time while maintaining the solutions in a constant state of agitation, the precipitated salts are continuously withdrawn and separated from the solvent by conventional means such as filtration, decantation, etc. The precipitate is then continuously charged to a drying apparatus such as an oven wherein the excess solvent is removed. After passage through the drying apparatus at an elevated temperature in excess of 100° C., the solid is continuously charged to a second reactor wherein it is contacted with the solution containing the modifier compound of the type herein set forth in greater detail. As in the first reaction zone, the solid is contacted with the solution of modified compound for a predetermined period of time and, after passage of this time period, is withdrawn from the second reactor. Again, the modified catalyst composite is separated from the solvent which may be either aqueous or organic in nature by conventional means, dried and thereafter passed to a calcination zone wherein it is calcined at a temperature of from 200° to 300° C. for a period of time sufficient to activate the catalyst and prepare it for use in a gas conversion reaction.

Some examples of gas conversion catalysts of the present invention will include a solid composite of copper, zinc and aluminum compounds containing tungsten; copper, zinc and aluminum compounds containing molybdenum; copper, zinc and aluminum compounds containing vanadium; copper, zinc and aluminum compounds containing chromium; copper, zinc and aluminum compounds containing titanium; copper, zinc and aluminum compounds containing zirconium; copper, zinc and aluminum compounds containing tantalum, etc.

The aforesaid gas conversion catalysts may be used in various gas conversion reactions. One type of gas conversion reaction in which the catalyst may be employed is the preparation of methanol from a feedstock comprising carbon monoxide and hydrogen which may also contain carbon dioxide. As was hereinbefore set forth, the feedstock which may be obtained from methanol gas or the gasification of coal may contain contaminants or catalyst poisons such as sulfur and/ or chlorine-containing compounds. The preparation of methanol may be effected by placing a catalyst composite of the present invention in an appropriate apparatus such as a reaction tube and charging the feedstock to the reactor which is maintained at the proper operating conditions of temperature and pressure for passage over the catalyst composite and continuously withdrawing the reaction product comprising methanol. The reaction conditions which may be employed to effect the production of methanol will include elevated temperatures in the range of from about 200° to about 400° C., a pressure in the range of from about 100 to about 1000 pounds per square inch (psig) and gaseous hourly space velocities which may range from about 500 to about 20,000. In the preferred embodiment of the invention, the preparation of methanol is effected in a continuous manner, the contact time of the catalyst and the feedstock being determined by the operating parameters which have been chosen to effect the reaction.

Inasmuch as the catalyst is in solid form, it is contemplated that the continuous method which is employed to obtain the methanol may be effected by utilizing the catalyst as a fixed bed in the reactor and charging the feedstock to the reactor so that the catalyst is contacted with the feedstock in either an upward or downward flow or by utilizing a moving bed type of operation in which the catalyst and the feedstock are contacted in the reactor either concurrently or countercurrently to each other.

The following examples are given for purposes of illustrating the novel gas conversion catalyst of the present invention and to a method for the preparation thereof. However, it is to be understood that the examples are given merely for purposes of illustration and that the present invention is not necessarily limited thereto.

EXAMPLE I

In this example, a conventional catalyst system was prepared by preparing aqueous solutions of copper nitrate, zinc nitrate and aluminum nitrate. The solutions were combined and thereafter heated to a temperature of about 60° C. A second solution of sodium carbonate dissolved in water was prepared, heated to 60° C. and the two solutions were admixed with vigorous mechanical stirring. The pH of the mixture was adjusted to 7.0 by the addition of sodium carbonate and aged for a period of 20 minutes at a temperature of 65° C. Upon completion of the aging period, the solution was filtered and the precipitate comprising copper-zinc-aluminum hydroxy-carbonate was dried at a temperature of 110° C. in an oven. The solid precipitate was treated with methyl alcohol which was evaporated and thereafter the catalyst composite was calcined in a tube furnace at a temperature of 260° C. in a flowing nitrogen atmosphere for a period of 4 hours. The catalyst was then crushed to 20-60 mesh, the final catalyst composite containing 42% by weight of the copper, 12% by weight of zinc, and 5.8% by weight of aluminum, the remainder being the carbonate composition of the salt.

To illustrate the catalytic activity of the catalyst, 1.9 grams thereof was placed in a fixed bed reactor, the reactor was heated to a temperature of 216° C. and a gaseous feed which consisted of 25.5% carbon monoxide, 64.4% hydrogen, 6% carbon dioxide and 3.9% argon was charged to the reactor at a gaseous hourly space velocity of 10,100 while operating at a pressure of 750 psig. In addition, the gaseous feed also contained a nominal amount of 0.2 ppm of sulfur as hydrogen sulfide with a similar level of chlorine impurities. The product which was recovered from the reaction consisted primarily of methanol in a yield of 99.4%. The original conversion of carbon monoxide plus carbon dioxide amounted to 26%. However, after 25 hours of reaction time, the conversion decreased to 18%, and after 45 hours to 13%.

EXAMPLE II

To illustrate the ability of the catalyst of the present invention to operate over a longer period of time without deactivating, a portion of the same catalyst base which was prepared in Example I above was used. As hereinbefore set forth, the solid catalyst composite was obtained by preparing aqueous solutions of copper nitrate, zinc nitrate and aluminum nitrate and combining the three solutions. The combined solutions were then heated to a temperature of about 60° C. and admixed with a second solution of aqueous potassium carbonate which had also been heated to 60° C. The admixture of the solutions was accompanied by a vigorous mechanical stirring of the solutions to ensure complete precipitation. After adjusting the pH of the mixture to 7.0, the mixture was aged for a period of 20 minutes at 65° C. Thereafter, the solution was filtered and the solid precipitate comprising copper-zinc-aluminum hydroxy carbonate was dried at a temperature of 110° C. in an oven for a period of 12 hours.

The solid catalyst composite was impregnated with a solution of tungstosilicic acid dissolved in methanol in a round bottom flask mounted on a rotary vacuum evaporator. After a rolling period of 30 minutes at room temperature, the flask and contents thereof were heated to a temperature of 35° C. under a reduced pressure of 300 torr which slowly evaporated the methanol. After evaporation of the methanol, the catalyst composite which was modified with tungsten was dried in an oven at 110° C. and calcined at a temperature of 260° C. in a flowing nitrogen atmosphere for a period of 12 hours. The final catalyst composite contained 48% by weight of copper, 15% by weight of zinc, 5.7% by weight of aluminum and 0.17% by weight of tungsten.

Into a fixed bed reactor was placed 1.9 grams of the catalyst, the reactor was heated to a temperature of 216° C. and a gaseous feed which consisted of 25.5% carbon monoxide, 64.4% hydrogen, 3.9% argon, with 0.2 ppm of sulfur and 0.2 ppm of chlorine impurity was charged to the reactor at a gaseous hourly spaced velocity of 10,100 at a pressure of 750 psig. The product which was recovered again consisted primarily of methanol in a yield of 99.4%. The reaction was permitted to proceed for a period of 95 hours. Carbon monoxide and carbon dioxide conversion was monitored during the test run, analysis determining that the original conversion of 23% dropped to 21% at 25 hours, 20% at 45 hours, 19% at 75 hours and 17% at 95 hours.

Comparison of the carbon monoxide and carbon dioxide conversion when utilizing the catalyst of the present invention, that is, a copper, zinc and aluminum composite which had been modified by the presence of tungsten to the catalyst described in Example I above showed that the activity of the catalyst was more active, even after twice as many hours on stream, as was the activity of the unmodified catalyst composite.

EXAMPLE III

In a manner similar to that hereinbefore set forth, a catalyst system may be prepared by admixing aqueous solutions of copper acetate, zinc acetate and aluminum acetate. In addition, a second solution of ammonium carbonate may be prepared and after both solutions are heated to a temperature of about 50° C., the solutions are combined while vigorously admixing the solutions by means of a mechanical stirring device. The pH of the combined solution may be adjusted to about 7.1 and after the precipitate is allowed to age at an elevated temperature of about 70° C., the solution may be filtered. The precipitate comprising copper-zinc-aluminum hydroxy-carbonate may then be dried at a temperature of 110° C. and water washed to remove any residual cations from the precipitate. Following this, the washed material may then be again dried at a temperature of 110° C. in an oven and broken up into a desired particle size.

The catalyst composite may then be impregnated with various solutions of a modifier such as molybdophosphoric acid, vandomanganic acid, chromium carbonyl, or titanium nitrate in a manner similar to that set forth in Example II. The impregnation of the catalyst composite may be effected in a rotary vacuum evaporator at an elevated temperature of about 50° C. and a reduced pressure in a range from about 100 to about 600 torr so as to slowly evaporate the solvent which has been employed to prepare the solution of the modified compound. After evaporation, the impregnated or modified catalyst composite may then be dried at a temperature of about 110° C. to remove any residual solvent and thereafter it may be calcined at a temperature of from about 200° to about 300° C. under a nitrogen blanket to produce the desired modified catalyst composite.

This catalyst composite may then be utilized as a gas conversion catalyst, one example of which being a methanol synthesis reaction in which a feedstock comprising carbon monoxide and hydrogen and, if so desired, carbon dioxide, may be passed over the catalyst at a temperature of about 220° C. and a pressure of about 700 psig using a gas hourly space velocity of about 10,000 to produce methanol.

We claim as our invention:

1. A catalyst for the production of methanol which comprises a solid composite of calcined compounds of copper, zinc and aluminum containing vanadium as a modifier.

2. The catalyst as set forth in claim 1 in which said vanadium modifier is present in said solid composite in an amount in the range of from about 0.01% to about 1% by weight of said composite.

* * * * *